United States Patent [19]
Fried

[11] Patent Number: 5,387,712
[45] Date of Patent: * Feb. 7, 1995

[54] PREPARATION OF AROMATIC ALKOXYALKANOIC ACIDS

[75] Inventor: Herbert E. Fried, Houston, Tex.

[73] Assignee: Shell Oil Company, Houston, Tex.

[*] Notice: The portion of the term of this patent subsequent to Dec. 29, 2009 has been disclaimed.

[21] Appl. No.: 187,360

[22] Filed: Jan. 26, 1994

Related U.S. Application Data

[63] Continuation of Ser. No. 981,039, Nov. 24, 1992, abandoned.

[51] Int. Cl.$^6$ .............................................. C07C 51/16
[52] U.S. Cl. ................................................... 562/420
[58] Field of Search ................................. 562/419, 420

[56] References Cited

U.S. PATENT DOCUMENTS

| | | | |
|---|---|---|---|
| 3,317,591 | 5/1967 | Schultz | 562/419 |
| 3,668,244 | 6/1972 | Strojny | 562/420 |
| 4,791,224 | 12/1988 | Sumner | 562/421 |
| 4,804,777 | 2/1989 | Sumner | 562/421 |
| 4,935,540 | 6/1990 | Sumner | 562/421 |
| 5,162,579 | 11/1992 | Fried | 562/538 |
| 5,166,422 | 11/1992 | Fried | 562/538 |
| 5,166,423 | 11/1992 | Fried | 562/538 |
| 5,175,359 | 12/1992 | Fried | 562/540 |
| 5,175,360 | 1/1992 | Fried | 562/538 |
| 5,179,218 | 1/1993 | Fried | 562/540 |

Primary Examiner—Michael L. Shippen
Attorney, Agent, or Firm—Pamela J. McCollough

[57] ABSTRACT

A process for the preparation of an aromatic alkoxyalkanoic acid by reacting the corresponding aromatic alkoxyalkanol with a stable free radical nitroxide in the presence of a $NO_x$-generating compound and an oxidant at a temperature in the range of from about 0° C. to about 100° C. and thereafter separating out the aromatic alkoxyalkanoic acid.

20 Claims, No Drawings

1

PREPARATION OF AROMATIC ALKOXYALKANOIC ACIDS

This is a continuation of application Ser. No. 981,039, filed Nov. 24, 1992, now abandoned.

FIELD OF THE INVENTION

This invention relates to a process for the preparation of aromatic alkoxyalkanoic acids by the oxidation of the corresponding aromatic alkoxyalkanols in the presence of a stable free radical nitroxide, a $NO_x$-generating compound and an oxidant.

BACKGROUND OF THE INVENTION

Aromatic alkoxyalkanols are useful as industrial surfactants and the corresponding aromatic alkoxyalkanoic acids may be useful as anionic detergents. The aromatic alkoxyalkanoic acids can be prepared in a two-step process by first reacting an aromatic alkanol with ethylene oxide and a suitable alkoxylation catalyst and thereafter converting the aromatic alkoxyalkanol to an alkoxyalkanolic acid.

Japanese Patent No. 50-96516, issued Jul. 31, 1975, discloses a process for the preparation of carboxylic acid salts by the liquid phase dehydrogenation of alcohols with caustic alkali in the presence of precious metal catalysts, including palladium. This process uses a relatively high temperature, 100° C.-270° C. These high temperatures can degrade the ether linkages especially in the highly ethoxylated alcohols.

It is known to use nitroxyl radicals/oxoammonium salts in the oxidation of primary alcohols to produce aldehydes and acids and alcohols to ketones. *Journal of Organic Chemistry*, vol. 52 (12), pp. 2559-2562: *Pure and Applied Chemistry*, vol. 62(2), 1990, pp. 217-222; *Journal of Organic Chemistry*, vol. 55, 1990, pp. 462-466. The primary products produced in these processes are aldehydes and the stoichiometrically consumed oxidant is hypochlorite.

It is generally more difficult to oxidize aromatic alkoxyalkanols than alkanols or primary alkoxyalkanols as it is difficult to oxidize aromatic alkoxyalkanols without splitting the molecular chain at the phenolic ether linkage and thereby producing a large proportion of undesired byproducts or having the aromatic ring undergo oxidation.

It would therefore be advantageous to produce aromatic alkoxyalkanoic acids in high yields and with high selectivities from aromatic alkoxyalkanols without producing large amounts of other products such as alkyl phenols, quinones, polyethylene glycols and oxidized polyethylene glycols.

It has been found that aromatic alkoxyalkanoic acids can be produced in high yields and with high selectivities without the formation of highly corrosive, difficult to separate, side-products by using catalytic amounts of a stable free radical nitroxide, a $NO_x$-generating compound and an oxidant.

SUMMARY OF THE INVENTION

This invention relates to a process for the preparation of an aromatic alkoxyalkanoic acid which comprises reacting the corresponding aromatic alkoxyalkanol with a stable free radical nitroxide having the formula:

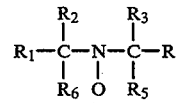

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$-$R_6$, are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of 0 or N, or (2) the

moiety and the

moiety individually are aryl, in the presence of a $NO_x$-generating compound and an oxidant at a temperature in the range of from about 0° C. to about 100° C. and thereafter separating out the aromatic alkoxyalkanoic acid.

DESCRIPTION OF THE PREFERRED EMBODIMENTS

The present process converts aromatic alkoxyalkanols to the corresponding aromatic alkoxyalkanoic acids by contacting the aromatic alkoxyalkanol with a stable free radical nitroxide in the presence of a $NO_x$-generating compound and an oxidant at a temperature in the range of from about 0° C. to about 100° C. and thereafter separating out the aromatic alkoxyalkanoic acid.

The aromatic alkoxyalkanol reactant suitably comprises one or more aromatic alkanols having a carbon number in the range of from about 6 to about 200, preferably from about 6 to about 30, and more preferably from about 14 to about 20, to which from about 1 to about 200 moles, preferably from about i mole to about 50 moles, and more preferably from about 1 mole to about 9 moles, of alkylene oxide per mole of aromatic alkanol has been added. The aromatic alkoxyalkanols are typically prepared by the reaction of an aromatic alkanol with alkylene oxide in the presence of a suitable alkoxylation catalyst to prepare a alkoxylate mixture, and the reaction of the resulting alkoxylate mixture in the presence of an acidic (e.g., Lewis acid) catalyst with sufficient additional alkylene oxide to produce a suitable alkanol alkoxylate mixture. Aromatic alkanols suitable for use in preparing the aromatic alkoxyalkanol reactant include $C_6$ to $C_{200}$, preferably $C_6$ to $C_{30}$ aromatic alkanols such as, for example, nonylphenol, octylphenol, dodecylphenol, pentadecylphenol, hexadecylphenol and phenol.

Aromatic alkoxyalkanols suitable for use in the present invention include phenol ethoxylates, nonyl phenol ethoxylates, octyl phenol ethoxylates, dodecyl phenol ethoxyl ates, pentadecyl phenol ethoxylate, hexadecyl phenol ethoxylates and the like, and mixtures of these aromatic alkoxy-alkanols. It is contemplated that the aromatic alkanols may have any number of substituents which do not interfere with the oxidation of the hydroxy group. Suitable substituents include alkyl, chloro, nitro, sulfonyl and the like. In a preferred embodiment, the aromatic alkoxyalkanol reactant is selected from the group consisting of nonylphenol ethoxylates, octylphenol ethoxylates, phenol ethoxylates and mixtures thereof, with nonylphenol ethoxyl ates and octyl phenol ethoxyl ates being particularly preferred. Examples of suitable aromatic alkoxyalkanols which are commercially available include IGEPAL CA and IGEPAL CO, trademarks of and sold by Rhone-Poulenc. TERGITOL NP, TRITON N and TRITON X, trademarks of and sold by Union Carbide, and SURFONIC N, a trademark of and sold by Texaco.

The process of the instant invention is particularly suited to ethoxylated aromatic alcohols with about 6 to about 200, preferably about 14 to about 20 carbon atoms. The number of such alkoxylate groups, ($CH_2CHRO$), wherein R is an alkyl group, ranges from 1 to about 20. In a preferred embodiment, the starting aromatic alkoxyalkanol is an ethoxylated aromatic alcohol which has had the unreacted alcohols and lower ethoxylates topped off in order to give an ethoxylate having about four ethylene oxide units per molecule.

The term "stable free radical nitroxide" as used herein shall mean a free radical nitroxide that can be prepared by conventional chemical methods and will exist long enough to be used in a subsequent chemical reaction or examined in a static system by normal methods of spectroscopy. Generally, the stable free radical nitroxides of the present invention have a half life of at least one year. The term "stable free radical" shall also be understood to include the precursor to a stable free radical from which the stable free radical may be produced in situ.

The stable free radical nitroxides, as used in the present process, are precursors to catalysts, i.e., oxoammonium salts, active for the oxidation of alkanols to the corresponding acids. These catalysts are generated in situ by the oxidation of a stable free radical nitroxide to an oxoammonium salt with an oxygen-containing oxidant. The stable free radical nitroxide can be obtained by the oxidation of amines or hydroxyl amines.

The stable free radical nitroxides which are suitable for use in the instant invention have the formula:

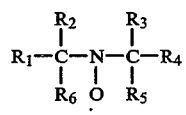
(III)

wherein each of $R_1$, $R_2$, $R_3$ and $R_4$ is an alkyl, aryl or heteroatom substituted alkyl groups and no hdyrogen is bound to the remaining valences on the carbon atoms bound to the nitrogen. As used herein, the term "alkyl" is meant to include cycloalkyl. The alkyl (or heteroatom substituted) groups R1–R4 may be the same or different, and preferably contain 1 to 15 carbon atoms. Preferable, $R_1$–$R_4$ are methyl, ethyl, or propyl groups.

In addition to hydrogen, the heteroatom substituents may include, halogen, oxygen, nitrogen and the like.

The remaining valences ($R_5$ and $R_6$) in formula III above may be satisfied by any atom or group except hydrogen which can bond covalently to carbon, although some groups may reduce the stabilizing power of the nitroxide and are undesirable. When $R_1$, $R_2$, $R_3$ and $R_4$ are each alkyl groups, however, at least one of R5 and R6 must be an aryl group. Preferably, $R_5$ and $R_6$ are substituted alkyl groups having 1 to about 15 carbon atoms wherein the substituent is selected from halogen, cyano, —COOR, wherein R is alkyl or aryl, —CONH2, —OCOC2H5, carbonyl, or alkenyl where the double bond is not conjugated with the nitroxide moiety, or alkyl groups of 1 to about 15 carbon atoms. $R_5$ and $R_6$ together may also form a ring of five carbon atoms and up to two heteroatoms, such as O or N. Examples of suitable compounds having the structure above and in which $R_5$ and $R_6$ form part of the ring are piperidinyl-1-oxyls and pyrrolidin-1-oxyls.

The

and the

moieties in formula III above can individually be aryl, i.e.,

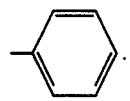

Examples of suitable compounds having the structure above in which the

and the

moieties are individually aryl are diphenylamine, phenyl tertiary butylamine, 3,3'-dimethyldiphenylamines, 2,2'-chlorodiphenylamine and the like. These compounds may be substituted with an substituents which do not interfere with the reaction.

In a preferred embodiment, the stable free radical nitroxide has the formula:

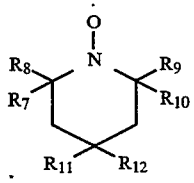

wherein each of $R_7$, $R_8$, $R_9$ and $R_{10}$ is an alkyl, aryl or heteroatom substituted alkyl group having 1 to about 15 carbon atoms and no hydrogen is bound to the remaining valences on the carbon atoms bound to the nitrogen, and each of $R_{11}$ and $R_{12}$ is alkyl, hydrogen, aryl or a substituted heteroatom. As used herein, the term "alkyl" is meant to include cycloalkyl. The alkyl (or heteroatom substituted) groups $R_7$-$R_{10}$ may be the same or different, and preferably contain 1 to 15 carbon atoms. Preferably, $R_7$-$R_{10}$ are methyl, ethyl, or propyl groups. In addition to hydrogen, the heteroatom substituents may include, halogen, oxygen, nitrogen and the like. Preferably, one of $R_{11}$ and $R_{12}$ is hydrogen, with the other one being a substituted heteroatom which does not interfere with the reaction. Suitable substituted heteroatoms include

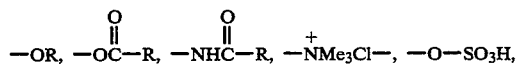

—O—polymer and the like.

In a particularly preferred embodiment, the nitroxide is selected from the group consisting of 2,2,6,6-tetramethyl-piperidine-1-oxyl, 4-hydroxy -2,2,6,6-tetramethyl-piperidine-1-oxyl, 4-pivolyl-2,2,6,6-tetramethyl -piperidine-1-oxyl, 2,2,6,6-tetramethyl-piperidine-1-oxyl-4-sulfate, 4-alkoxy -2,2,6,6-tetramethyl-piperidine-1-oxyl, and mixtures thereof, with 2,2,6,6-tetramethyl-piperidine-1-oxyl, 2,2,6,6-tetramethyl-piperidine-1-oxyl-4-sulfate, and 4-alkoxy-2,2,6,6-tetramethyl-piperidine-1-oxyl being especially preferred.

The $NO_x$-generating compound in the present process is typically selected from the group consisting of an alkali metal nitrosodisulfonate, nitric acid and mixtures thereof, with nitric acid being preferred. However, any compound which serves to generate $NO_x$ during the course of the reaction and which does not interfere with the reaction would be suitable. While not wishing to be bound by any particular theory, it is believed that nitrogen oxides ($NO_x$) are generated in the reaction and are required to generate the active catalytic species.

The alkali metal nitrosodisulfonate suitable for use as a $NO_x$-generating compound can be any alkali metal nitrosodisulfonate although potassium nitrosodisulfonate is preferred. As used herein, the term "alkali metal" is used as a descriptor of the elements Group IA of the Periodic Table of the Elements (Li, Na, K, Rb, Cs, Fr). The alkali metal nitrosodisulfonate is typically dissolved in water prior to being added to the reaction mixture although it can be added as a solid after all of the other reactants have been added.

As used herein, the term "nitric acid" refers to nitric acid, fuming nitric acid or nitrous acid generated by contacting a nitrate or nitrite salt such as, for example, an alkali metal salt, a tetraalkylammonium salt, an alkaline earth salt or a rare earth salt, with a strong acid such as, for example, a mineral acid. The nitric acid suitable for use as a $NO_x$-generating compound in the present invention typically has a concentration in the range of from about 50 percent to about 100 percent, preferably about 70 percent. Generally, an amount of nitric acid in the range of from about 5 mole percent to about 100 mole percent, basis the moles of starting aromatic alkoxyalkanol is utilized. The nitric acid is typically added to the reaction mixture after all of the other reactants have been added.

The oxidants suitable for use in the instant invention are those compounds which are capable, in the presence of a $NO_x$-generating compound, of oxidizing the stable free radical nitroxide to the oxoammonium salt. Suitable oxidants include oxygen-containing gases such as pure oxygen and oxygen in air. Whereas pure oxygen can is preferred to accomplish the desired conversion, the oxygen can also be diluted with an inert gas such as nitrogen, helium, argon, or other similar gas. While air can be used as the oxidant, the reaction rate is much slower. For purposes of increasing the reaction rate, higher O2 pressures such as, for example, 1000 psig can be utilized. In a preferred embodiment, pure oxygen is used as the oxidant and it is bubbled into the reaction solution. In another embodiment, air can be bubbled through the reaction solution.

The amounts and concentrations of the reactants utilized in the process of the instant invention can vary within wide ranges. The amount of stable free radical nitroxide is typically in the range of from about 1 mole percent to about 50 mole percent, preferably from about 5 mole percent to about 20 mole percent, basis the number of moles starting aromatic alkoxyalkanol. Generally, the amount of $NO_x$-generating compound used is in the range of from about 5 mole percent to about 100 mole percent, basis the number of moles of aromatic alkoxyalkanol.

The process of the present invention is typically conducted under mild conditions, with good results being obtained using a temperature in the range of from about 0° C. to about 100° C., preferably about 20° C. to about 80° C., and most preferably, about 40° C. to about 60° C. Reaction pressures are not critical although higher pressures can result in increased reaction rates. Pressures in the range of from about atmospheric pressure up to about 1000 psig can be employed with good results.

The process of the instant invention can be carried out either batchwise or continuously, using a stirrer equipped reactor or other well known contacting technique to achieve adequate mixing. Preferred reaction conditions, e.g., temperature, pressure, flow rates, etc., vary somewhat depending on the specific nitroxide utilized and on the concentration of the. nitroxide.

The process of the instant invention can be carried out in a variety of ways. For example, 0.032 moles of aromatic alkoxyalkanol, and 0.006 moles percent by weight of the nitroxide, may be added to the reaction vessel, followed by the addition of 0.011 moles of 70 percent nitric acid and bubbling $O_2$ through the reaction mixture. Following the reaction, the product may be separated from the reaction mixture using conventional procedures such as extraction using a suitable extraction solvent such as, for example, ethyl acetate; evaporation wherein the solvent is stripped from the reaction mixture by using heat or vacuum. Phase separation of the final product mixture takes place at 100° C. with water. The reaction product can be purified by a number of conventional means such as high temperature water washing or catalytic hydrogenation.

Depending upon process conditions and the nitroxide used, the yields of aromatic alkoxyalkanoic acid obtained by this invention can be greater than about 98% of starting material being converted. The products produced by the instant process can be used in a variety of industrial or household detergent applications. For example, deinking or heavy duty laundry liquids or powders.

The ranges and limitations provided in the instant specification and claims are those which are believed to particularly point out and distinctly claim the present invention. It is, however, understood that other ranges and limitations which perform substantially the same function in the same or substantially the same manner to obtain the same or substantially the same result are intended to be within the scope of the instant invention as defined by the instant specification and claims.

The process of this invention will be further described by the following embodiments which are provided for illustration and are not to be construed as limiting the invention.

ILLUSTRATIVE EMBODIMENTS

EXAMPLE 1

12.3 Grams of a nonylphenol ethoxylate having an average of 4.1 ethylene oxide units per molecule of alcohol, 1.0 gram of 2,2,6,6-tetramethyl-piperidine-1-oxyl, 25 milliliters of dichloromethane and 1 gram of 70 percent nitric acid were charged to a 100 milliliter round bottomed flask. $O_2$ was bubbled through this mixture at ambient pressure. The reaction temperature was held at 35° C. over a 3-hour period. The results are presented in Table I.

EXAMPLE 2

12.3 Grams of a nonylphenol ethoxylate having an average of 4.1 ethylene oxide units per molecule of alcohol, 1 gram of 2,2,6,6-tetramethyl-piperidine-1-oxyl, 0.5 grams of Aliquot 336, I gram of potassium nitrosodisulfonate, 2 grams of water and 50 milliliters of acetonitrile were charged to a 100 milliliter round bottomed flask containing 50 milliliters of dichloromethane. $O_2$ was bubbled through this mixture at ambient pressure. The reaction was held at 20° C. over a 16-hour period. The results are presented in Table I.

COMPARATIVE EXAMPLE A

Comparative Example A was carried out in a manner similar to Example 1 except that no nitroxide was used. The results are presented in Table I.

COMPARATIVE EXAMPLE B

Comparative Example B was carried out in a manner similar to Example except that no nitric acid was used. The results are presented in Table I.

As can be seen in Table I, nitroxide and nitric acid are necessary for the oxidation of the aromatic alkoxyalkanol to proceed.

TABLE I

Oxidation of Aromatic Alkoxyalkanols to Aromatic Alkoxyalkanoic Acids

|  | % Conversion | % Selectivity to Acids |
|---|---|---|
| Example 1 | >99 | >99 |
| Example 2 | 81 | >99 |
| Comparative Example A | <5 | 0 |
| Comparative Example B | 0 | 0 |

What is claimed is:

1. A process for the preparation of an aromatic alkoxyalkanoic acid which comprises reacting the corresponding alkoxylated aromatic alcohol which has a carbon number in the range of from about 14 to about 20 and from about 1 mole to about 9 moles of alkylene oxide per mole of alkoxylated aromatic alkanol with a stable free radical nitroxide having the formula:

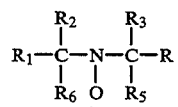

wherein (1) (a) each of $R_1$, $R_2$, $R_3$ and $R_4$ is an alkyl, aryl or heteroatom substituted alkyl group having 1 to about 15 carbon atoms, and (b) $R_5$ and $R_6$ (i) each is an alkyl group having 1 to about 15 carbon atoms provided that $R_1$–$R_6$ are not all alkyl groups, or a substituted alkyl group having 1 to about 15 carbon atoms wherein the substituent is hydrogen, cyano, —$CONH_2$, —OCOCH, $OCOC_2H_5$, carbonyl, alkenyl wherein the double bond is not conjugated with the nitroxide moiety, or —COOR wherein R of the —COOR group is alkyl or aryl, or (ii) together form part of a ring that contains 5 carbon atoms and up to two heteroatoms of 0 or N, or (2) the

moiety and the

moiety individually are aryl, in the presence of a $NO_x$-generating compound selected from the group consisting of an alkali metal nitrosodisulfonate, nitric acid and mixtures thereof, and an oxidant comprising an oxygen-containing gas at a temperature in the range of from about 0° C. to about 100° C. and thereafter separating out the aromatic alkoxyalkanoic acid.

2. The process of claim 1 wherein the alkoxylated aromatic alcohol is selected from the group consisting of nonylphenol ethoxylate, phenol ethoxylates, octylphenol ethoxylates, dodecylphenol ethoxylates, pentadecylphenol ethoxyl ates, hexadecyl phenol ethoxyl ates and mixtures thereof.

3. The process of claim 2 wherein the alkoxylated aromatic alcohol is selected from the group consisting of nonylphenol ethoxylates, octylphenol ethoxylates and mixtures thereof.

4. The process of claim 1 wherein the stable free radical nitroxide has the formula:

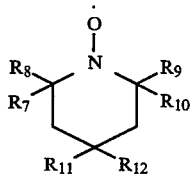

wherein each of $R_7$, $R_8$, $R_9$ and $R_{10}$ is an alkyl, aryl or heteroatom substituted alkyl group having 1 to about 15 carbon atoms and each of $R_{11}$ and $R_{12}$ is alkyl, hydrogen, aryl or a substituted heteroatom.

5. The process of claim 4 wherein the stable free radical nitroxide is selected from the group consisting of 2,2,6,6-tetramethyl-piperidine-1-oxyl, 4-hydroxy-2,2,6,6-tetramethyl-piperidine-1-oxyl, 4-pivolyl-2,2,6,6-tetramethyl-piperidine-1-oxyl, 2,2,6,6-tetramethyl-piperidine-1-oxyl-4sulfate, 4-oxo-2,2,6,6-tetramethyl-piperidine,4-alkoxy-2,2,6,6-tetra-methyl-piperidine and mixtures thereof.

6. The process of claim 5 wherein the stable free radical nitroxide is selected from the group consisting of 2,2,6,6-tetra methyl-piperidine-1oxyl, 2,2,6,6-tetramethyl-piperidine-1-oxyl-4-sulfate, 4-alkoxy-2, 2,6,6-tetramethyl -piperidine-1-oxyl and mixtures thereof.

7. The process of claim 1 wherein said $NO_x$-generating compound is nitric acid.

8. The process of claim 7 wherein said nitric acid has a concentration in the range of from about 50 percent to about 100 percent.

9. The process of claim 8 wherein said nitric acid has a concentration of about 70 percent.

10. The process of claim 7 wherein said $NO_x$-generating compound is an alkali metal nitrosodisulfonate.

11. The process of claim 10 wherein said alkali metal nitrosodisulfonate is potassium nitrosodisulfonate.

12. The process of claim 1 wherein the amount of $NO_x$-generating compound is in the range of from about 5 mole percent to about 100 mole percent, basis the number of moles alkoxylated aromatic alcohol.

13. The process of claim 1 wherein said is contacted with said stable free radical nitroxide, followed by the addition thereto of said $NO_x$-generating compound and said oxidant.

14. The process of claim 13 wherein the amount of stable free radical nitroxide is in the range of from about 1 mole percent to about 50 mole percent, basis the number of moles of alkoxylated aromatic alcohol.

15. The process of claim 17 wherein the amount of stable free radical nitroxide is in the range of from about 5 mole percent to about 20 mole percent, basis the number of moles of alkoxylated aromatic.

16. The process of claim 13 wherein-the amount of $NO_x$-generating compound is in the range of from about 5 mole percent to about 100 mole percent, basis the number of moles of alkoxylated aromatic alcohol.

17. The process of claim 1 wherein said oxygen containing gas is selected from the group consisting of pure oxygen and air.

18. The process of claim 17 wherein said oxygen-containing gas is pure oxygen.

19. The process of claim 1 wherein said process is carried out at a temperature in the range of from about 20° C. to about 70° C. and at atmospheric pressure.

20. The process of claim 19 wherein said process is carried out at a temperature in the range of from about 40° C. to about 60° C. and at atmospheric pressure.

* * * * *